(12) United States Patent
Boyle et al.

(10) Patent No.: US 6,506,203 B1
(45) Date of Patent: Jan. 14, 2003

(54) LOW PROFILE SHEATHLESS EMBOLIC PROTECTION SYSTEM

(75) Inventors: William J. Boyle, Fallbrook, CA (US); Richard S. Stack, Chapel Hill, NC (US)

(73) Assignee: Advanced Cardiovascular Systems, Inc., CA (US)

(*) Notice: Subject to any disclaimer, the term of this patent is extended or adjusted under 35 U.S.C. 154(b) by 139 days.

(21) Appl. No.: 09/740,560

(22) Filed: Dec. 19, 2000

(51) Int. Cl.$^7$ .............................................. A61M 29/00
(52) U.S. Cl. ...................................................... 606/200
(58) Field of Search ................... 606/200, 159, 606/151, 157, 213, 215

(56) References Cited

U.S. PATENT DOCUMENTS

| | | |
|---|---|---|
| 4,723,549 A | 2/1988 | Wholey et al. |
| 4,997,435 A | 3/1991 | Demeter |
| 5,100,425 A | 3/1992 | Fischell et al. |
| 5,158,548 A | 10/1992 | Lau et al. |
| 5,437,632 A | 8/1995 | Engleson |
| 5,814,064 A | 9/1998 | Daniel et al. |
| 5,827,324 A | 10/1998 | Cassell et al. |
| 5,846,251 A | 12/1998 | Hart |
| 5,911,734 A | 6/1999 | Tsugita et al. |
| 5,980,555 A | 11/1999 | Barbut et al. |
| 5,989,281 A | 11/1999 | Barbut et al. |
| 6,066,149 A * | 5/2000 | Samson et al. |
| 6,096,053 A * | 8/2000 | Bates |
| 6,264,672 B1 * | 7/2001 | Fisher |

* cited by examiner

*Primary Examiner*—Ismael Izaguirre
(74) *Attorney, Agent, or Firm*—Fulwider Patton Lee & Utecht, LLP

(57) ABSTRACT

A system used in a blood vessel when an interventional procedure is being performed in a stenosed or occluded region, which is capable of enabling a support device and filter supported thereon, to be inserted into the blood vessel and to cross the stenosis therein in a low profile without a sheath extending thereabout. The filter is adapted to filter the blood in the blood vessel. The system is further capable of enabling the support device and filter to be positioned distal to the interventional procedure site, and to be activated to expand at the distal location so as to enable the filter to capture any embolic material that may be created and released into the bloodstream during the interventional procedure. The system is also capable of enabling the support device and filter to be activated to contract to a return profile for enabling the filter to retain the embolic material captured therein and the removal of the support device and filter from the blood vessel. The system includes a filter, adapted to be deployed distal to the interventional procedure site, and to pass blood therethrough and capture embolic material which may be released into the blood in the blood vessel during the interventional procedure. A support device is adapted to support the filter, and to retain a low profile so as to enable the filter to be inserted into and cross the stenosis in the blood vessel, to a position distal to the interventional procedure site, without a sheath extending about the filter and the support device. The support device is further adapted to deform for expansion thereof into open position to enable the filter to capture embolic material, and to enable the collapsing thereof to retain the embolic material captured in the filter, and to enable removal of the support device and the filter. The system also includes a mechanism, connected to the support device, adapted to be activated so as to enable the support device to deform for expansion thereof.

25 Claims, 2 Drawing Sheets

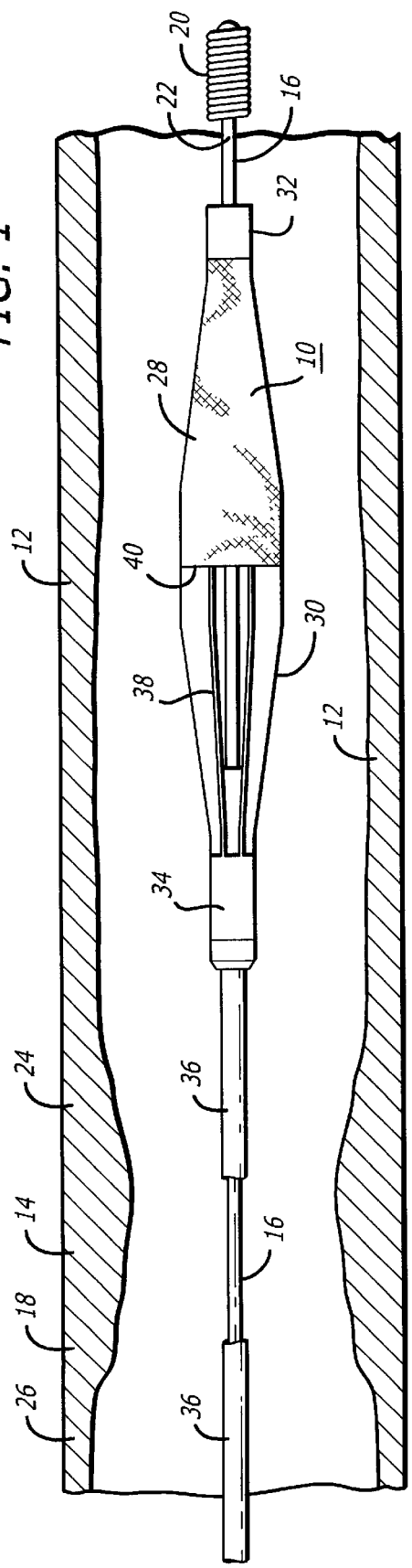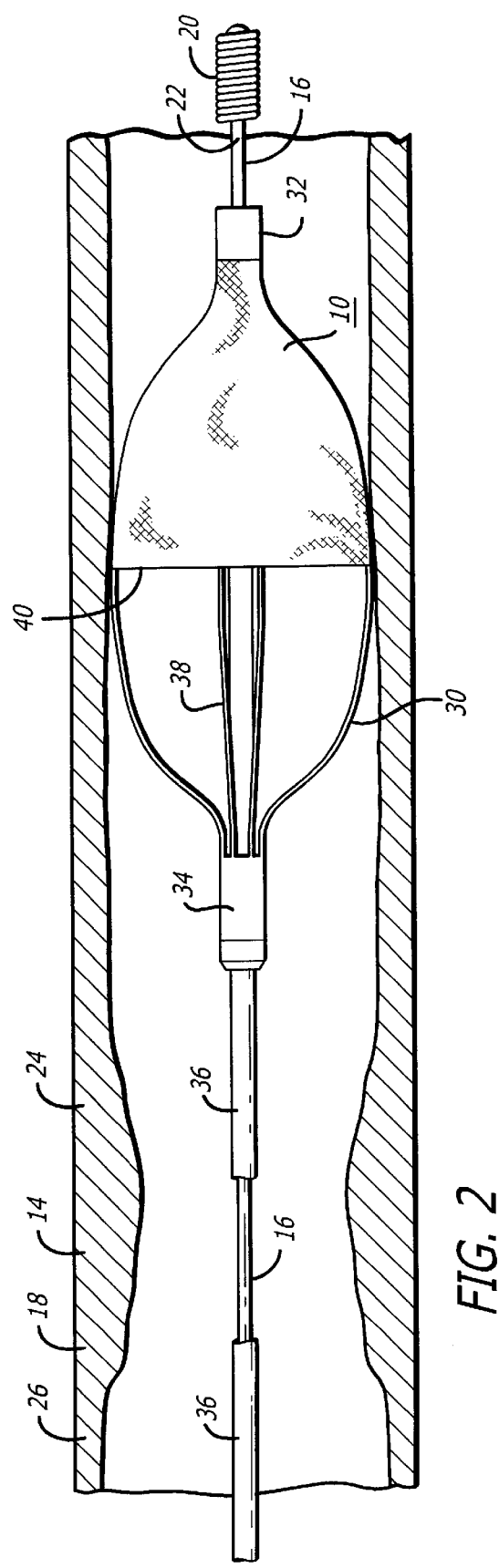

LOW PROFILE SHEATHLESS EMBOLIC PROTECTION SYSTEM

BACKGROUND OF THE INVENTION

The present invention relates generally to a system which can be used when an interventional procedure is being performed in a stenosed or occluded region of a blood vessel, to enhance the insertion, deployment, and removal of a low profile sheathless support device and filter for filtering the blood in a blood vessel so as to capture embolic material that may be created and released into the bloodstream during the procedure. The system of the present invention is particularly useful when performing balloon angioplasty, stenting procedures, laser angioplasty or atherectomy in critical vessels, such as the carotid, renal, and saphenous vein graft arteries, where the release of embolic debris into the bloodstream could possibly occlude the flow of oxygenated blood to the brain or other vital organs which can cause devastating consequences to the patient.

A variety of non-surgical interventional procedures have been developed over the years for opening stenosed or occluded blood vessels in a patient caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Another procedure is laser angioplasty which utilizes a laser to ablate the stenosis by super heating and vaporizing the deposited plaque. Atherectomy is yet another method of treating a stenosed blood vessel in which a cutting blade is rotated to shave the deposited plaque from the arterial wall. A vacuum catheter may be used to capture the shaved plaque or thrombus from the blood stream during this procedure.

In another widely practiced procedure, the stenosis can be treated by placing a device known as a stent into the stenosed region to hold open and sometimes expand the segment of the blood vessel or other arterial lumen. Stents are particularly useful in the treatment or repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

In the past, stents typically have fallen into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanium (NiTi) alloys, which will automatically expand from a compressed state when the stent is advanced out of the distal end of the delivery catheter into the body lumen. Such stents manufactured from self-expandable materials allow for phase transformations of the material to occur, contributing to the expansion and contraction of the stent.

The above non-surgical interventional procedures, when successful, avoid the necessity of major surgical operations. However, there is one common problem associated with all of these non-surgical procedures, namely, the potential release of embolic debris into the bloodstream which can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, particles are not always fully vaporized and may enter the bloodstream.

When any of the above-described procedures are performed for example in the carotid arteries, the release of emboli into the circulatory system can be extremely dangerous to the patient. Debris that is carried by the bloodstream to distal vessels of the brain may cause these cerebral vessels to occlude, resulting in a stroke, and in some cases, death. Therefore, although carotid percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such procedures in the carotid arteries a high-risk proposition.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could cause problems to the patient's vasculature.

Further techniques which have had some limited success include the placement of a filter or trap downstream from the treatment site to capture embolic debris before it reaches the smaller blood vessels downstream. However, there have been problems associated with filtering systems, particularly during the insertion, expansion, deployment, and removal of the filter within the blood vessel. The filter needs to cross the stenosis in as small a profile as possible so as to clear the stenosis and prevent damage thereto. Previous designs have employed an outer catheter called a "sheath" to keep these filters constrained prior to delivery beyond the stenosis. This outer catheter necessarily increases the profile of the device which could in and of itself create embolic complications as this high profile device is forced through the stenosis. After crossing the stenosis and being positioned distal to the interventional procedure site, the filter needs to be deployed, and after the interventional procedure has been performed, the filter needs to be removed with the captured embolic material therein, in an efficient and effective manner.

What has been needed is a reliable system and method for treating stenosis in blood vessels which reduces the profile and improves the stenosis crossing characteristics of a filter, for crossing the stenosis to a position distal to the interventional procedure site for deployment of the filter. The system and method should further be capable of enabling effective filter deployment at the position distal to the interventional procedure site, and for removal from the position distal to the interventional procedure site, for capturing embolic debris in the bloodstream that can cause blockage in vessels at downstream locations. The system and method should be capable of filtering embolic debris which may be released into the bloodstream during the treatment to the vessel, and yet allow a sufficient amount of oxygenated blood to flow past the filtering device to supply vital organs downstream from the treatment site. The system and method should be relatively easy for a physician to use and should provide a nearly failsafe filtering system capable of removing embolic debris released into the bloodstream. Moreover, such a system should be relatively easy to deploy and remove from the patient's vasculature. The inventions disclosed herein satisfy these and other needs.

SUMMARY OF INVENTION

The present invention provides a system and method for capturing and retaining embolic debris from a blood vessel which may be created during the performance of a therapeutic interventional procedure, such as a balloon angioplasty or stenting procedure, in order to prevent the embolic debris from lodging and blocking blood vessels downstream from the interventional site. The present invention is particularly useful while performing an interventional procedure in vital arteries, such as the carotid arteries, in which critical downstream blood vessels can become blocked with embolic debris, including the main blood vessels leading to the brain or other vital organs. As a result, the present invention provides the physician with a higher degree of confidence that any and all embolic debris is being collected and removed from the blood vessel when performing high-risk interventional procedures.

The present invention is deployed in the blood vessel at a location distal to the area of treatment in the interventional procedure site, passes the blood therethrough to enable blood to flow past the filter, and filters the blood to capture and retain any embolic debris which may be created during the interventional procedure.

In one aspect of the present invention, the system includes a support device, and a filter supported thereon, to span across the inside of the blood vessel and to capture and retain embolic material. The emboli-capturing system of the present invention directs the blood flow through the area where the interventional procedure is to be performed and through the filter located distal to the interventional site, which is designed to capture and retain friable plaque deposits. Additionally, the present invention allows blood to flow past the filter to provide a substantially continuous stream of blood to the organs located downstream.

In an embodiment of the present invention, the system includes a filter which can be deployed within the blood vessel for filtering blood flow past the expandable member at a location distal downstream to the interventional procedure site. The filter is adapted to be supported on a low profile support device, so as to enable efficient and effective insertion of the filter into the blood vessel and crossing of the stenosis to a location distal to the interventional procedure site, without a sheath extending thereabout. The filter and support device are further adapted to be effectively expanded for deployment thereof at the location distal to the interventional procedure site, and to be efficiently collapsed to retain the embolic material captured therein and to enable removal thereof from the blood vessel.

In a particular embodiment of the present invention, the system comprises a filter, adapted to be deployed distal to the interventional procedure site, and to pass blood therethrough and capture embolic material which may be released into the blood in the blood vessel during the interventional procedure. A support device is adapted to support the filter, and to retain a low profile so as to enable the filter to be inserted into and cross the stenosis in the blood vessel, to a position distal to the interventional procedure site, without a sheath extending about the filter and the support device. The support device is further adapted to deform for expansion thereof into open position to enable the filter to capture embolic material, and to be collapsed so as to retain the embolic material captured in the filter, and to enable removal of the support device and the filter. The system also includes a mechanism for enabling the support device to deform for expansion thereof into the open position, to enable the filter to capture embolic material.

Other features and advantages of the present invention will become more apparent from the following detailed description of the preferred embodiments of the invention, when taken in conjunction with the accompanying exemplary drawings.

BRIEF DESCRIPTION OF THE DRAWINGS

FIG. 1 is an elevational view, partially in section, depicting a first embodiment of the present invention disposed within the internal carotid artery of a patient, including a low profile sheathless support device and filter in unexpanded condition.

FIG. 2 is an elevational view, partially in section, of the first embodiment shown in FIG. 1, wherein the support device and filter are in expanded condition.

DETAILED DESCRIPTION OF THE PREFERRED EMBODIMENTS

Figure 3:
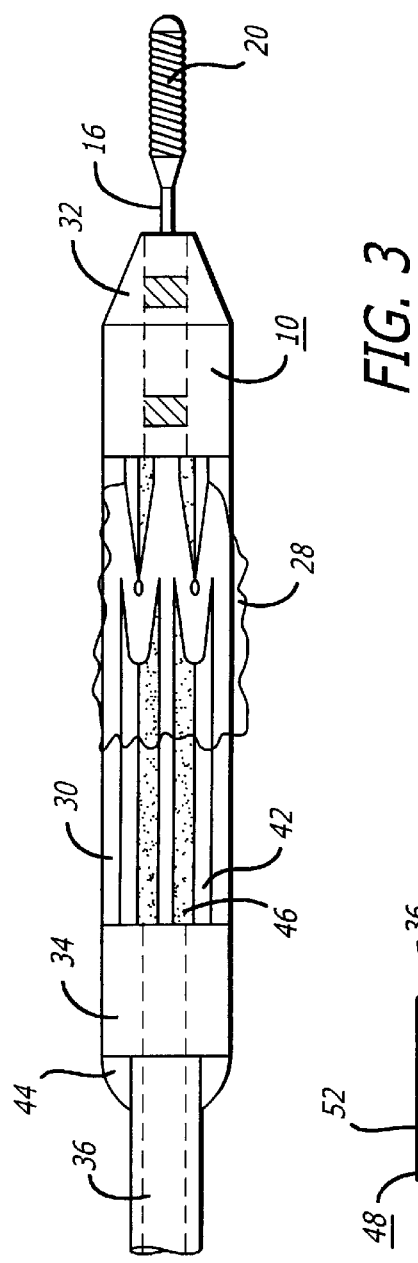
FIG. 3 is an elevational view, partially in section, of a second embodiment of the invention, including a low profile sheathless support device and filter in unexpanded condition.

One aspect of the invention is an improved system and method for efficiently and effectively enabling a therapeutic interventional procedure to be performed in a blood vessel at the site of a stenosis, adapted to enable a support device for a filter to retain a low profile, so as to enable the filter to be inserted into and cross a stenosis in the blood vessel without a sheath extending about the filter and the support device. The support device is also adapted to deform for expansion thereof into open position, to enable the filter to capture embolic material, and to collapse into closed position to enable removal of the filter with the embolic material captured therein. It is adapted to filter the blood in the blood vessel, so as to pass blood therethrough, and capture embolic material which may be released into the blood vessel during the interventional procedure. The embodiments of the improved system and method are illustrated and described herein by way of example only and not by way of limitation. While the present invention is described in detail as applied to the carotid arteries of the patient, those skilled in the art will appreciate that it can also be used in other body lumens as well, such as the coronary arteries, renal arteries, saphenous veins and other peripheral arteries. Additionally, the present invention can be utilized when performing any one of a number of interventional procedures, such as stenting, balloon angioplasty, laser angioplasty or atherectomy.

Referring now to the drawings, wherein like reference numerals denote like or corresponding parts throughout the drawing figures, and particularly in an exemplary embodiment of the invention as shown in FIGS. 1–2, a system 10 is provided for enabling an interventional procedure to be performed in a blood vessel 12 at an area of treatment 14. The system 10 is adapted to be atraumatic. It includes a core wire 16 adapted to enable the system 10 to be positioned distal to the area of treatment 14. As shown in FIGS. 1–2, the system 10 may be placed within the carotid artery 18 or other blood vessel of the patient, and may be guided into position by the core wire 16. The core wire 16 may include a coiled tip 20 at a distal end 22 of the core wire 16. The carotid artery 18 may have the area of treatment therein 14, which may comprise the interventional procedure site, wherein atherosclerotic plaque 24 may have built up against the inside wall 26 which decreases the diameter of the carotid artery 18. As a result, blood flow may be diminished through this area.

The therapeutic interventional procedure may comprise implanting an expandable interventional instrument at the interventional procedure site 14, to press the build-up of plaque 24 of the stenosis against the inside wall 26, to increase the diameter of the occluded area 14 of the artery 18, and to help restore sufficient flow of blood to the downstream vessels leading to the brain. The expandable interventional instrument may not only help increase the diameter of the occluded area, but may help prevent restenosis in the area of treatment 14. The expandable interventional instrument may be adapted to be expanded and deployed at the interventional procedure site 14.

The system 10 includes a filter 28, adapted to filter the blood in the blood vessel 12, so as to pass blood therethrough and capture embolic material which may be released in the blood vessel 12 during the interventional procedure. The core wire 16 is adapted to enable the filter 28 to be placed within the carotid artery 18 or other blood vessel of the patient and guided into position distal to the area of treatment 14.

The system 10 further includes a cage support device 30, adapted to support the filter 28. The cage support device 30 may be further adapted retain a low profile so as to enable the filter 28 to be inserted into and cross the stenosis in the blood vessel 12, to a position distal to the interventional procedure site 14, without a sheath extending about the filter 28 and the cage support device 30. The cage support device 30 includes a distal end 32, and a proximal end 34. The system 10 also includes a hypotube 36, comprising a hollow tube through which the core wire 16 is adapted to extend and to be movable relative thereto. The distal end 32 of the cage support device 30 is adapted to be secured to the distal end 22 of the core wire 16, and the proximal end 34 of the cage support device 30 is adapted to be secured to the hypotube 36. The extended core wire 16 is adapted to enable the cage support device 30 to retain an ultra low profile for crossing the stenosis. The cage support device 30 may also be adapted to be activated by pulling the core wire 16, to plastically deform the cage support device 30 for expansion thereof into open position, to enable the filter 28 supported thereon to capture embolic material. The system 10 may further include a recovery sheath, adapted to extend over the hypotube 36, and to collapse the expanded cage support device 30 as it moves in the distal direction therealong, to retain the embolic material captured in the filter 28, and to enable removal of the cage support device 30 and the filter 28.

The cage support device 30 may be comprised for example of a plastically deformable material, or of stainless steel. The plastically deformable material may comprise for example titanium or tantalum, a laminate composite structure of a super elastic material such as for example nickel titanium and stainless steel, or a radiopaque material such as for example tantalum. The composite structure may be co-drawn by means of tubing processing technology, or alternative layers of materials may be applied by means of plating or metal deposition technology. The outside diameter of the support device 30 may be ground to provide longitudinal binding characteristics. The support device 30 may alternatively be comprised of an elastic polymer material, selected to provide radial strength, elastic material properties, and composite radiopacity under fluoroscopy.

The cage support device 30 may include a plurality of struts 38, adapted to support the filter 28. Portions of the filter 28 are adapted to extend through the struts 38 of the cage support device 30, and the extending portions of the filter 28 comprise flaps adapted to be configured so as to extend around the outside of the cage support device 30. The cage support device 30 may further include a support ring 40, adapted to support the filter 28. The filter 28 may include a hydrophilic coating, and may comprise an outer membrane for the cage support device 30. The distal end 32 of the cage support device 30 may include a hydrophilic coating.

Figure 4:
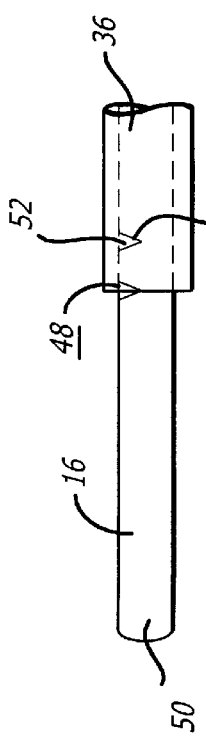
FIG. 4 is a n elevational fragmentary view of the second embodiment shown in FIG. 3, depicting a locking mechanism therein.

In the embodiment of the invention as shown in FIGS. 3–4, the cage support device 30 may comprise a basket, which includes an expandable portion 42. The basket 30 is attached to the hypotube 36 at the proximal end 34 of the basket 30 by an attaching element 44. The expandable portion 42 of the basket 30 is adapted to enable the basket 30 to retain its low profile during insertion thereof through the vasculature, and to plastically deform upon activation thereof. The filter 28 is adapted to be crimped into the expandable portion 42 of the basket 30. The expandable portion 42 of the basket 30 may include longitudinal slots 46 therein, for enabling flexible deforming thereof. The attaching element 44 may be comprised of a biocompatible material such as for example stainless steel, titanium, or superelastic nickel titanium alloys. The attaching element 44 may also be comprised of adhesive or solder.

The system 10 may further include a locking mechanism 48, as shown in FIG. 4, located at a proximal end 50 of the core wire 16, which, in a first position thereof, is adapted to retain the cage support device 30 and the filter 28 in the low profile position, and, in a second position thereof, is adapted to secure and lock the cage support device 30 and the filter 28 in the plastically deformed open position thereof. The locking mechanism 48 is further adapted to be released at the completion of the interventional procedure, so as to enable the recovery sheath to collapse the cage support device 30 and the filter 28 for retrieval thereof. The locking mechanism 48 may comprise a projection 52 in a proximal end 54 of the hypotube 36, and a complimentary recessed portion 56 in the core wire 16 adapted to enable the projection 52 of the hypotube 36 to engage therewith.

Figure 5:
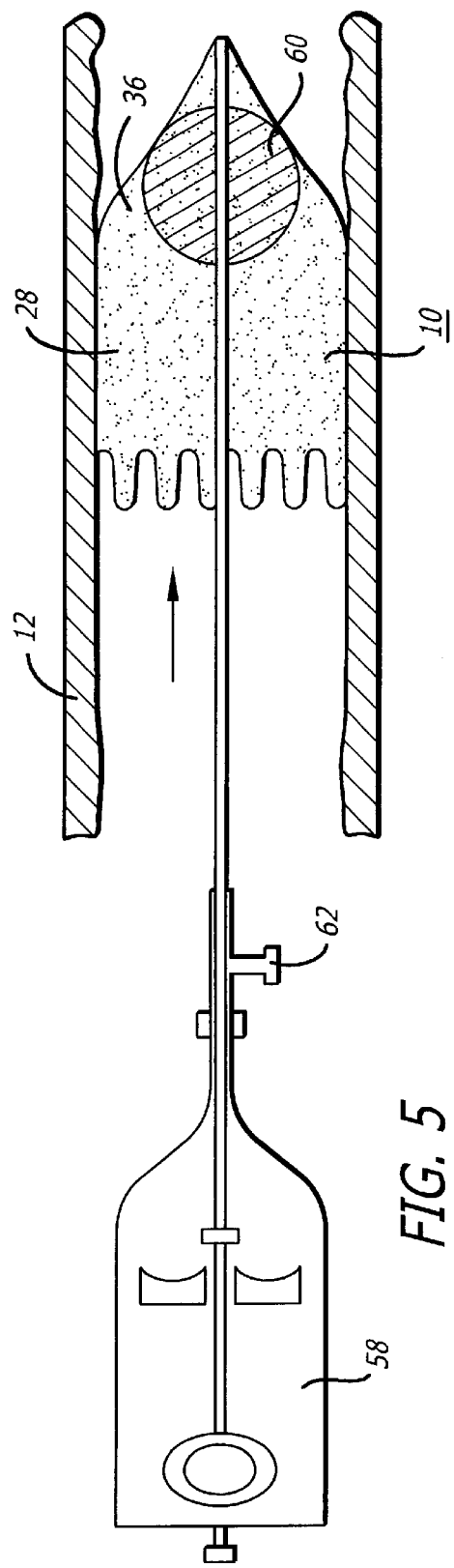
FIG. 5 is an elevational view, partially in section, of a third embodiment of the present invention, wherein the support device and filter are in expanded condition.

In the embodiment of the invention as shown in FIG. 5, the locking mechanism 48 may include a plunger mechanism 58 for enabling the inflation of a small balloon 60, comprised of an easily stretched material such as a compliant elastic, so as to expand the plastically deformable cage support device 30 and the filter 28 crimped on top thereof. The plunger mechanism 58 may include a detachable lock position thereof. The cage support device 30 may further include a handle 62, for connecting the plunger mechanism 58 to the inflatable balloon 60. The system 10 may further include an inflator such as a syringe with a saline solution, for enabling inflation of the inflatable balloon 60. The inflator may include a port.

In use, in the embodiments of the invention as illustrated in FIGS. 1–4, the system 10 may be positioned in the patient's vasculature utilizing any one of a number of different methods. In one preferred method of positioning, the cage support device 30 and the filter 28 supported thereon may be placed in the blood vessel 12 by utilizing the core wire 16, to the distal end 22 of which the cage support device 30 and the filter 28 are secured. The core wire 16 is inserted into the patient's vasculature and manipulated by the physician to the area of treatment 14 to cross the stenosis in the blood vessel 12 and place the cage support device 30 and the filter 28 thereon at a location distal to the area of treatment 14, with the cage support device 30 and filter 28 retaining the low profile and without a sheath extending thereabout. After the cage support device 30 and the filter 28 are in place, the core wire 16 may be activated by being pulled in the proximal direction, thereby pulling the distal end 32 of the cage support device 30 secured to the core wire 16, so as to compress the cage support device against the proximal end 34 thereof secured to the hypotube 36. Such movement of the core wire 16 and the distal end 32 of the cage support device 30 causes the cage support device 30 to deform plastically and expand into an open position, which causes the filter 28 supported thereon to expand, so as to enable the filter 28 to capture embolic material which may be released in the blood vessel 12 during the interventional procedure.

After the interventional procedure is performed, a recovery sheath may be extended about the hypotube 36 to the cage support device 30 and the filter 28, and may be pushed in the distal direction so as to collapse the cage support device 30 and the filter 28 with the captured embolic material therein. The recovery sheath, with the collapsed cage support device 30 and the filter 28 and captured embolic material, may then be retrieved from the interventional procedure site 14.

As seen in the embodiment of the invention in FIGS. 3–4, upon activation of the core wire 16, the longitudinal slots 46 may assist the expansion of the cage support device 30 and the filter 28 which may plastically deform to expand into open position, to enable the filter 28 to capture embolic material which may be released in the blood vessel 12 during the interventional procedure. The hypotube 36 and the proximal end 34 of the cage support device 30 secured thereto may initially be locked to the core wire 16 with the distal end 32 of the cage support device 30 secured thereto, so as to retain the ultra low profile of the cage support device 30, by rotating the proximal end 50 of the core wire 16 such that a projection 52 of the hypotube 36 engages a recess 56 in the core wire 16. To lock the cage support device 30 in the expanded position thereof, the proximal end 50 of the core wire 16 is rotated to enable engagement of a projection 52 of the hypotube 36 with a recess 56 in the core wire 16. Upon extension of the recovery sheath along the hypotube 36, the core wire 16 is rotated to unlock the core wire 16 from the hypotube 36, to enable the cage support device 30 to collapse within the recovery sheath.

As seen in the embodiment of the invention in FIG. 5, upon activation of the plunger 58 to exert pressure through the handle 62 and an inflation lumen in the hypotube 36, the inflatable balloon 60 may expand into open position, expanding the filter 28 to enable the capture therein of embolic material which may be released during the interventional procedure.

It should be appreciated that the particular embodiments set forth above of the low profile sheathless cage support device 30 and the filter 28 supported thereon are capable of being positioned in the blood vessel 12. However, other forms of the cage support device 30 and filter 28 may be utilized with the present invention without departing from the spirit and scope of the invention. For example, the cage support device 30 and filter 28 may further be comprised of other forms of material. Additionally, while the cage support device 30 and filter 28 are shown as in various shapes in the embodiments herein, they can be formed in any one of a number of different shapes depending upon the construction desired.

Further, the various components may be joined by suitable adhesives such as acrylonitrile based adhesives or cyanoacrylate based adhesives. Heat shrinking or heat bonding may also be employed where appropriate. Plastic-to-plastic or plastic-to-metal joints can be effected by a suitable acrylonitrile or cyanoacrylate adhesive. Variations can be made in the composition of the materials to vary properties as needed. Based on the present disclosure, other adhesives and applications are known to one skilled in the art.

In view of the foregoing, it is apparent that the system and method of the present invention enhances substantially the effectiveness of performing interventional procedures by enabling a support device for the filter to retain a low profile so as to enable the filter to be inserted into and cross a stenosis in the blood vessel without a sheath extending thereabout. It further substantially enhances the interventional procedure effectiveness by enabling the support device for the filter to deform for expansion thereof to enable the filter to capture embolic material, and to return to a profile upon contraction thereof into closed position to enable removal of the filter with the embolic material captured therein. Further modifications and improvements may additionally be made to the system and method disclosed herein without the departing from the scope of the invention. Accordingly, it is not intended that the invention be limited by the specific description of the embodiments.

What is claimed:

1. A system for capturing embolic material which may be released into a blood vessel during a therapeutic interventional procedure at the site of a stenosis, comprising:

a filter, adapted to be deployed distal to the interventional procedure site, and to pass blood therethrough and capture embolic material which may be released into the blood in the blood vessel during the interventional procedure;

a support device, adapted to support the filter, to retain a low profile position responsive to positive retention thereof in the low profile position so as to enable the filter to be inserted into and through the blood vessel, and to cross the stenosis therein, to a position distal to the interventional procedure site, without a sheath extending about the filter and the support device, and adapted to deform for expansion thereof into an open position, to enable the filter to capture embolic material, responsive to positive deforming for expansion thereof into the open position and retention therein; and a mechanism for enabling the support device to be positively retained in the low profile position thereof and to be positively deformed for expansion thereof into the open position and retention therein, to enable the filter to be inserted into and through the blood vessel and to cross the stenosis therein, and to expand to capture embolic material.

2. The system of claim 1, wherein the system is atraumatic.

3. The system of claim 1, wherein the support device is adapted to retain an ultra low profile for crossing the stenosis.

4. The system of claim 1, wherein the support device is comprised of a plastically deformable material.

5. The system of claim 1, wherein the filter includes a distal end member, the support device includes a proximal end member, and the mechanism comprises a hollow tube, which includes a distal end, to which the proximal end member of the support device is adapted to be secured, and a core wire, adapted to be movable within the hollow tube, which extends through the distal end member of the filter and to which the distal end member of the filter is adapted to be secured.

6. The system of claim 1, wherein the support device comprises a balloon, and the mechanism comprises a hollow tube, which includes a distal end, and which has a port in the distal end, and wherein the balloon is adapted to extend about the distal end of the hollow tube, and to be inflated by pressure exerted through the hollow tube and the port in the distal end thereof.

7. The system of claim 6, wherein the balloon is comprised of a compliant polymeric material.

8. The system of claim 1, wherein the support device is comprised of a super elastic material.

9. The system of claim 1, wherein the s support device is comprised of a polymer material.

10. The system of claim 1, wherein the support device includes a plurality of rails, adapted to connect to the filter.

11. The system of claim 1, wherein the support device includes a plurality of support struts, adapted to support the filter.

12. The system of claim 11, wherein the filter includes a proximal end, the plurality of struts each include a distal end, and the support device further includes a support ring, to which the distal end of each of the plurality of struts is secured, and to which the proximal end of the filter is secured, adapted to positively support the filter.

13. The system of claim 1, wherein the support device includes a support ring, adapted to support the filter.

14. The system of claim 1, wherein the support device is comprised of stainless steel.

15. The system of claim 1, further comprising a recovery sheath for enabling retrieval of the support device and the filter upon completion of the interventional procedure.

16. The system of claim 1, further comprising a locking mechanism for locking the support device and the filter in the low profile position thereof.

17. The system of claim 16, wherein the locking mechanism is further adapted to lock the support device and the filter in the open position thereof.

18. The system of claim 1, wherein the filter is adapted to be crimped into the support device.

19. The system of claim 1, wherein the support device includes longitudinal slots therein, for enabling flexible deforming thereof.

20. A system for capturing embolic material which may be released into a blood vessel during a therapeutic interventional procedure at the site of a stenosis, comprising:

a filter, adapted to be deployed distal to the interventional procedure site, and to pass blood therethrough and capture embolic material which may be released into the blood in the blood vessel during the interventional procedure;

means for supporting the filter, adapted to retain a low profile so as to enable the filter to be inserted into and cross the stenosis in the blood vessel, to a position distal to the interventional procedure site, without a sheath extending about the filter and the support device, to deform for expansion thereof into an open position to enable the filter to capture embolic material; and a mechanism for enabling the support device to deform for expansion thereof into the open position to enable the filter to capture embolic material.

21. The system of claim 20, wherein the supporting means are adapted to retain an ultra low profile for crossing the stenosis.

22. The system of claim 20, wherein the supporting means are comprised of a plastically deformable material.

23. A method of capturing embolic material which may be released into a blood vessel during a therapeutic interventional procedure at the site of a stenosis, in a system which comprises a filter, adapted to be deployed distal to the interventional procedure site, and to pass blood therethrough and capture embolic material which may be released into the blood in the blood vessel during the interventional procedure, a support device, adapted to support the filter, to retain a low profile position responsive to positive retention thereof in the low profile position so as to enable the filter to be inserted into and through the blood vessel and cross the stenosis therein in the blood vessel, to a position distal to the interventional procedure site, without a sheath extending about the filter and the support device, and adapted to deform for expansion thereof into an open position to enable the filter to capture embolic material responsive to positive deforming for expansion thereof into the open position and retention therein, and a mechanism for enabling the support device to be positively retained in the low profile position thereof and to be positively deformed for expansion thereof into the open position and retention therein to enable the filter to be inserted into and through the blood vessel and cross the stenosis therein and to expand to capture embolic material, wherein the method comprises:

inserting the support device and the filter supported thereon into the blood vessel and crossing the stenosis in the blood vessel, to a position distal to the interventional procedure site, with the support device retaining the low profile and without a sheath extending about the filter; and activating the mechanism so as to enable the support device to deform and expand into the open position to enable the filter to capture embolic material.

24. The method of claim 23, wherein the filter includes a core wire, to which the filter is adapted to be secured, further comprising activating the core wire so as to enable the support device to deform to the return profile upon contracting thereof into closed position, to enable removal of the filter and the embolic material captured therein.

25. The method of claim 23, wherein the support device is comprised of a plastically deformable material, farther comprising plastically deforming the support device to expand into the open position.

* * * * *